US012589116B2

(12) United States Patent
Kim et al.

(10) Patent No.: US 12,589,116 B2
(45) Date of Patent: Mar. 31, 2026

(54) METHOD FOR PRODUCING UMBILCAL CORD BLOOD-DERIVED STEM CELL WITH ENHANCED EFFICACY

(71) Applicant: KANGSTEM BIOTECH CO., LTD., Seoul (KR)

(72) Inventors: Mijin Kim, Gyeonggi-do (KR); Jong Chan Ahn, Gyeonggi-do (KR); Seunghee Lee, Seoul (KR); Kwang-Won Seo, Gyeonggi-do (KR); Kyung-Sun Kang, Seoul (KR)

(73) Assignee: KANGSTEM BIOTECH CO., LTD., Seoul (KR)

( * ) Notice: Subject to any disclaimer, the term of this patent is extended or adjusted under 35 U.S.C. 154(b) by 715 days.

(21) Appl. No.: 17/786,015

(22) PCT Filed: Dec. 16, 2020

(86) PCT No.: PCT/KR2020/018485
§ 371 (c)(1),
(2) Date: Jun. 16, 2022

(87) PCT Pub. No.: WO2021/125808
PCT Pub. Date: Jun. 24, 2021

(65) Prior Publication Data
US 2023/0051601 A1     Feb. 16, 2023

(30) Foreign Application Priority Data

Dec. 16, 2019     (KR) ........................ 10-2019-0168248

(51) Int. Cl.
*A61K 38/17*     (2006.01)
*A61K 35/28*     (2015.01)
*C12N 5/0775*     (2010.01)

(52) U.S. Cl.
CPC .......... *A61K 35/28* (2013.01); *A61K 38/1709* (2013.01); *C12N 5/0665* (2013.01); *C12N 2533/30* (2013.01); *C12N 2533/52* (2013.01)

(58) Field of Classification Search
CPC ........ C12N 2533/52; C12N 2506/1369; C12N 5/0665
See application file for complete search history.

(56) References Cited

U.S. PATENT DOCUMENTS

2017/0226479 A1     8/2017     Bafja et al.

FOREIGN PATENT DOCUMENTS

| KR | 10-0744445 | B1 | 8/2007 |
| KR | 10-2009-0010646 | A | 1/2009 |
| KR | 10-1575226 | B1 | 12/2015 |
| KR | 20170133288 | A | 12/2017 |
| WO | 2017-204518 | A1 | 11/2017 |

OTHER PUBLICATIONS

Hashi CK, Zhu Y, Yang GY, Young WL, Hsiao BS, Wang K, Chu B, Li S. Antithrombogenic property of bone marrow mesenchymal stem cells in nanofibrous vascular grafts. Proc Natl Acad Sci U S A. Jul. 17, 2007;104(29):11915-20. doi: 10.1073/pnas.0704581104. Epub Jul. 5, 2007. PMID: 17615237; PMCID: PMC1924591. (Year: 2007).*
(2012) Application Forum: xsRapid Analysis of Human Adipose-Derived Stem Cells and 3T3-L1 Differentiation Toward Adipocytes Using the Scepter™ 2.0 Cell Counter, BioTechniques, 53:2, 109-111 (Year: 2012).*
Kang BJ, Kim H, Lee SK, Kim J, Shen Y, Jung S, Kang KS, Im SG, Lee SY, Choi M, Hwang NS, Cho JY. Umbilical-cord-blood-derived mesenchymal stem cells seeded onto fibronectin-immobilized polycaprolactone nanofiber improve cardiac function. Acta Biomater. Jul. 2014; 10(7):3007-17. (Year: 214).*
Li, Y., Liao, C., & Tjong, S. C. (2019). Electrospun Polyvinylidene Fluoride-Based Fibrous Scaffolds with Piezoelectric Characteristics for Bone and Neural Tissue Engineering. Nanomaterials, 9(7), Article 952. (Year: 2019).*
Augustine, R., Dan, P., Sosnik, A. et al. Electrospun poly(vinylidene fluoride-trifluoroethylene)/zinc oxide nanocomposite tissue engineering scaffolds with enhanced cell adhesion and blood vessel formation. Nano Res. 10, 3358-3376 (2017). (Year: 2017).*
Ribeiro C, Panadero JA, Sencadas V, Lanceros-Méndez S, Tamaño MN, Moratal D, Salmerón-Sánchez M, Gómez Ribelles JL. Fibronectin adsorption and cell response on electroactive poly(vinylidene fluoride) films. Biomed Mater. Jun. 2012;7(3):035004. (Year: 2012).*
Parssinen, Jenita et al. "Enhancement of adhesion and promotion of osteogenic differentiation of human adipose stem cells by poled electroactive poly(vinylidene flouoride)." J. Biomed Mater Res Part A, Mar. 2015, vol. 103A, Issue 3, pp. 919-928.
Wang, Hongwu et al. "Immunological characteristics of human umbilical cord mesenchymal stem cells and the therapeutic effects of their transplantion on hyperglycemia in diabetic rats." International journal of molecular medicine vol. 33,2 (2014): 263-70. doi:10.3892/ijmm.2013.1572.
Lin Manping et al., Biomaterials, vol. 162, p. 170-182, XP085355505 (2018).
Patricia Rico et al., Advanced Functional Materials, vol. 26, p. 6563-6573, XP072405638 (2016).
Asghari Sana Farzin et al., Cytotechnology, vol. 69, p. 617-630, XP036275273 (2017).

(Continued)

*Primary Examiner* — Fereydoun G Sajjadi
*Assistant Examiner* — Qinhua Gu
(74) *Attorney, Agent, or Firm* — Edwin S. Flores; Daniel J. Chalker; Chalker Flores, LLP

(57)     ABSTRACT

Disclosed is a method for producing a stem cell with enhanced efficacy, a stem cell produced thereby, and a method for treating a disease using the same.
According to the present invention, sizes of stem cells may be reduced and proliferation ability, differentiation potency, migration ability, and angiogenic potential of stem cells may be significantly enhanced by applying a culturing method provided herein. Thus the present invention may be usefully applied to development of therapeutic agents using stem cells.

10 Claims, 13 Drawing Sheets

Specification includes a Sequence Listing.

(56)  References Cited

OTHER PUBLICATIONS

Ribeiro C et al., Biomedical Materials, vol. 7 p. 035004, XP093111665 (2012).
Hung C_H et al., Biomaterials, vol. 27, p. 4461-4469, XP027951276 (2006).
Jeon Byeong-Min et al., Development & Reproduction, vol. 24, p. 135-147, XP093109657 (2020).
Extended European Search Report, EP 20902522.0 dated Jan. 12, 2024.
Wolfgang Wagner et al., "Comparative characteristics of mesenchymal stem cells from human bone marrow, adipose tissue, and umbilical cord blood" Experimental Hematology 33 (2005) 1402-1416.

* cited by examiner

Plate (x2000)          Membrane (x2000)

| Cell diameter (µm) | P4 | P5 | |
|---|---|---|---|
| | Plate | Plate | Membrane |
| Lot1 | 14 | 19.2 | 16.4 |
| Lot2 | 13.5 | 18.4 | 15 |

```
                        SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Synthetic: OCN F

<400> SEQUENCE: 1
agcaaaggtg cagcctttgt                                                20

<210> SEQ ID NO 2
<211> LENGTH: 19
<212> TYPE: DNA
<213> ORGANISM: Artificial Sequence
<220> FEATURE:
<223> OTHER INFORMATION: Synthetic: OCN R

<400> SEQUENCE: 2
gcgcctgggt ctcttcact                                                 19

<210> SEQ ID NO 3
<211> LENGTH: 20
<212> TYPE: DNA
<213> ORGANISM: Artificial Sequence
<220> FEATURE:
<223> OTHER INFORMATION: Synthetic: Osterix F

<400> SEQUENCE: 3
tggccatgct gactgcagcc                                                20

<210> SEQ ID NO 4
<211> LENGTH: 20
<212> TYPE: DNA
<213> ORGANISM: Artificial Sequence
<220> FEATURE:
<223> OTHER INFORMATION: Synthetic: Osterix R

<400> SEQUENCE: 4
tgggtaggcg tcccccatgg                                                20

<210> SEQ ID NO 5
<211> LENGTH: 23
<212> TYPE: DNA
```

-continued

<213> ORGANISM: Artificial Sequence
<220> FEATURE:
<223> OTHER INFORMATION: Synthetic: PPARgamma F

<400> SEQUENCE: 5
caggaaagac aacagacaaa tca                                        23

<210> SEQ ID NO 6
<211> LENGTH: 21
<212> TYPE: DNA
<213> ORGANISM: Artificial Sequence
<220> FEATURE:
<223> OTHER INFORMATION: Synthetic: PPARgamma R

<400> SEQUENCE: 6
ggggtgatgt gtttgaactt g                                          21

<210> SEQ ID NO 7
<211> LENGTH: 20
<212> TYPE: DNA
<213> ORGANISM: Artificial Sequence
<220> FEATURE:
<223> OTHER INFORMATION: Synthetic: LPL F

<400> SEQUENCE: 7
agacacagct gaggacactt                                            20

<210> SEQ ID NO 8
<211> LENGTH: 20
<212> TYPE: DNA
<213> ORGANISM: Artificial Sequence
<220> FEATURE:
<223> OTHER INFORMATION: Synthetic: LPL R

<400> SEQUENCE: 8
gcacccaact ctcatacatt                                            20

<210> SEQ ID NO 9
<211> LENGTH: 21
<212> TYPE: DNA
<213> ORGANISM: Artificial Sequence
<220> FEATURE:
<223> OTHER INFORMATION: Synthetic: Col2 F

<400> SEQUENCE: 9
cgtccagatg accttcctac g                                          21

<210> SEQ ID NO 10
<211> LENGTH: 19
<212> TYPE: DNA
<213> ORGANISM: Artificial Sequence
<220> FEATURE:
<223> OTHER INFORMATION: Synthetic: Col2 R

<400> SEQUENCE: 10
tgagcagggc cttcttgag                                             19

<210> SEQ ID NO 11
<211> LENGTH: 22
<212> TYPE: DNA
<213> ORGANISM: Artificial Sequence
<220> FEATURE:
<223> OTHER INFORMATION: Synthetic: Aggrecan F

<400> SEQUENCE: 11
ctgcattcca cgaagctaac ct                                         22

-continued

```
<210> SEQ ID NO 12
<211> LENGTH: 19
<212> TYPE: DNA
<213> ORGANISM: Artificial Sequence
<220> FEATURE:
<223> OTHER INFORMATION: Synthetic: Aggrecan R

<400> SEQUENCE: 12
gacgcctcgc cttcttgaa                                                                    19
```

METHOD FOR PRODUCING UMBILCAL CORD BLOOD-DERIVED STEM CELL WITH ENHANCED EFFICACY

CROSS-REFERENCE TO RELATED APPLICATIONS

This application is the National Stage of International Application No. PCT/KR2020/018485, filed on Dec. 16, 2020 claiming the priority of KR 10-2019-0168248, filed on Dec. 16, 2019, the content of each of which is incorporated by reference herein.

TECHNICAL FIELD OF THE INVENTION

The present invention relates to a method for producing a stem cell with enhanced efficacy, a stem cell produced thereby, and a method for treating a disease using the same.

BACKGROUND OF THE INVENTION

Stem cells are undifferentiated cells at stages prior to differentiation obtainable from embryonic, fetal, and adult tissues and have characteristics of self-renewal capacity, differentiation potency, and immortality. Stem cells may be classified into pluripotent, multipotent, and unipotent stem cells according to differentiation potency thereof. Since adult stem cells having multipotency are relatively free from the risk of cancerization, immunorejection, and ethical concerns compared to embryonic stem cells having pluripotency and induced pluripotent stem cells (IPSCs), extensive research thereon and development thereof as therapeutic agents have been in progress. Particularly, umbilical cord blood-derived mesenchymal stem cells (UCB-MSCs) which are mesenchymal stem cells derived from blood of newborn babies which circulates through a cardiovascular system of a fetus during pregnancy and is available from a placenta and an umbilical cord after childbirth. After research reports showing that UCB-MSCs have superior proliferation ability to that of stem cells derived from other tissues were published, UCB-MSCs have drawn considerable attention in various fields of study such as in the medical field. Particularly, as stem cells separated from discarded tissues, UCB-MSCs have a high value in terms of low donor's burden and recycling of medical waste.

Therapeutic effects of UCB-MSCs in models of wounds, diabetes, and heat infraction in which the UCB-MSCs are used as therapeutic agents have been reported in many papers (Wang, H., Qiu, X., Ni, P., Qiu, X., Lin, X., Wu, W. Ma, L. (2014). Immunological characteristics of human umbilical cord mesenchymal stem cells and the therapeutic effects of their transplantation on hyperglycemia in diabetic rats. International Journal of Molecular Medicine, 33, 263-270, et al). Therefore, UCB-MSCs have a commercial value as a therapeutic agent. However, since amounts of UCB-MSCs obtained at the early stage are limited, subculture is essential. However, characteristics of stem cells are lost during the subculture, for example, the ability to proliferate and differentiate decreases and cellular senescence progresses, according to conventional cell culture technologies, and thus there are difficulties in mass production and development of therapeutic agents for industrial use.

SUMMARY OF THE INVENTION

Technical Problem

The present inventors have developed a novel method for culturing stem cells capable of increasing efficacy of the stem cells and confirmed that the produced stem cells have superior efficacy to that of stem cells produced according to conventional culturing methods, thereby completing the present invention.

Technical Solution

An object of the present invention is to provide a method for enhancing efficacy of stem cells, the method including culturing the stem cells in a membrane coated with fibronectin.

Another object of the present invention is to provide a method for producing a cell therapy product, the method including obtaining stem cells with enhanced efficacy by culturing the stem cells in a membrane coated with fibronectin.

Another object of the present invention is to provide a cell therapy product including: the obtained stem cells, a culture broth thereof, or at least one of the stem cells and a substance derived from the culture broth, as an active ingredient, and a method for treating a disease using the same.

Advantageous Effects

According to the present invention, sizes of stem cells may be reduced and proliferation ability, differentiation potency, migration ability, and angiogenic potential of stem cells may be significantly enhanced by applying a culturing method provided herein, and thus the present invention may be usefully applied to development of therapeutic agents using umbilical cord blood-derived mesenchymal stem cells.

BRIEF DESCRIPTION OF THE DRAWINGS

FIG. 4a shows osteogenic differentiation potency, FIG. 4b shows adipogenic differentiation potency, and FIG. 4c shows chondrogenic differentiation potency.

DETAILED DESCRIPTION OF THE INVENTION

Figure 1:
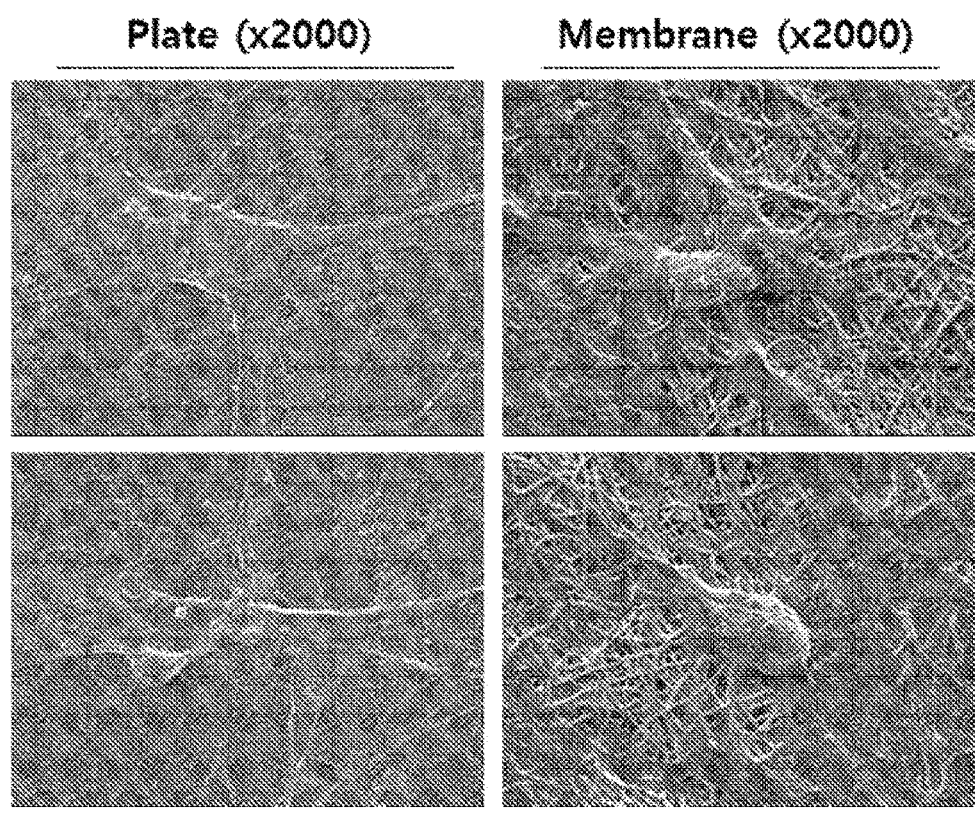
FIG. 1 shows sizes of umbilical cord blood-derived mesenchymal stem cells in an attached state according to culturing conditions.

The present invention will be described in detail. Meanwhile, each description and embodiment disclosed in the present invention may be applied to herein to different descriptions and embodiments. In other words, all combinations of various components disclosed in the present invention are included within the scope of the present invention. Furthermore, the scope of the present invention should not be limited by the descriptions provided below.

Also, those skilled in the art will recognize or be able to ascertain, using no more than routine experimentation, many equivalents to specific embodiments of the present invention. Such equivalents are intended to be encompassed in the scope of the following claims.

An aspect of the present invention provides a method for enhancing efficacy of stem cells, the method including culturing the stem cells in a membrane coated with fibronectin.

The culturing step may refer to "3D culture" in which cells are cultured in a 3D cell culture structure, and the membrane may be used as a support for culturing cells in the 3D culture. As used herein, the term "support for culturing cells" may also be referred to as "scaffold" indicating a physical support enabling test tube culture, in vitro culture, or transplantation of cells or tissues.

The membrane is not limited as long as the membrane is used as a scaffold for 3D cell culture. For example, fibers constituting the membrane may be derived from at least one polymer selected from polyurethane, a polyurethane copolymer, cellulose acetate, cellulose, acetate butyrate, a cellulose derivative, styrene-acrylonitrile (SAN), polyacrylonitrile (PAN), poly(vinyl acetate) (PVAc), polyvinylpyrrolidone (PVP), polyvinyl alcohol (PVA), poly-ethylene oxide (PEO), polyacrylic acid (PAA), hydroxypropyl cellulose (HPC), polymethylmethacrylate (PMMA), polyfurfuryl alcohol (PPFA), polystyrene (PS), a polystyrene copolymer, polyaniline (PANI), polyvinylchloride (PVC), poly(vinylidene fluoride) (PVDF), polyethylene terephthalate (PET), polypropylene (PP) or polyethylene (PE), and polyimide, without being limited thereto. In an embodiment, the membrane may be a membrane containing poly(vinylidene fluoride) (PVDF) fibers, i.e., "PVDF membrane".

The membrane may be a film formed of PVDF by electrospinning. Additionally, the membrane may be coated with a protein required for culturing cells, e.g., fibronectin, without being limited thereto.

The culturing may be suspension culture or attachment culture and the stem cells cultured according to the method of the present invention may include both suspension cultured cells and attachment cultured cells. As used herein, the term "suspension culture" refers to a type of cell culture in which cells are cultured in a state of floating in a culture medium without being attached to a certain surface. In this case, a certain number of cells may aggregate to form cell mass and proliferate.

The culture medium used in the culturing step may include all culture media for culturing stem cells commonly used in the art. As used herein, the "culture medium" refers to a composition containing essential components required for cell growth and proliferation in vitro, and any culture medium commonly used in the art for culturing stem cells may be used without limitation. For example, any commercially available culture medium such as KSB-3, Dulbecco's Modified Eagle's Medium (DMEM), Minimal Essential Medium (MEM), Basal Medium Eagle (BME), RPMI 1640, Dulbecco's Modified Eagle's Medium: Nutrient Mixture F-10 (DMEM/F-10), Dulbecco's Modified Eagle's Medium: Nutrient Mixture F-12 (DMEM/F-12), α-Minimal Essential Medium (α-MEM), Glasgow's Minimal Essential Medium (G-MEM), Isocove's Modified Dulbecco's Medium (IMDM), and KnockOut DMEM, and any artificially synthesized culture medium may be used, without being limited thereto. In addition, any culture medium modified by appropriately adding or removing components required for the culture medium may also be used.

The culture medium of the present invention may generally include a carbon source, a nitrogen source, and trace elements and may further include an amino acid, an antibiotic, and the like. The culture medium for culturing may or may not include serum as circumstances demand. In addition, the culture medium for culturing may include a serum replacement instead of serum, without being limited thereto.

The culturing step may be performed for 72 hours or less, specifically 60 hours or less, 48 hours or less, or 36 hours or less, but is not limited thereto, and the culturing time may be appropriately adjusted within a range not to reduce the efficacy of the stem cells.

The culturing step may be performed at a temperature of 20° C. to 45° C., specifically, 25° C. to 40° C., more specifically, 30° C. to 40° C., but is not limited thereto, and may be appropriated adjusted within a range not to reduce the efficacy of the stem cells.

In the present invention, the "enhancement of stem cell efficacy" may include at least one of an increase in growth factor expression, regulation of expression of a factor involved in a signaling pathway, a decrease in size of stem cells, an improvement in proliferation ability, an improvement in differentiation potency, an improvement in immunoregulatory ability, an improvement in migration ability, an improvement in engraftment capacity, an improvement in angiogenic potential, and an increase in secretion of bio-nanoparticles. However, the embodiment is not limited thereto and the enhancement of stem cell efficacy may include any enhancement of properties useful for development of treatment methods or therapeutic agents for diseases using stem cells. For example, the enhancement of stem cell efficacy may also include a decrease in immunogenicity, an increase in stemness, suppression of cell viability reduction, and a decrease in cellular senescence.

In an embodiment, the enhancement of stem cell efficacy may involve a decrease in size of stem cells. In addition, the enhancement of stem cell efficacy may include a change in characteristics of the stem cells in accordance with the decrease in size of the stem cells.

The enhancement of stem cell efficacy may refer to enhancement compared to that of stem cells cultured without using the culturing method of the present invention.

In an embodiment, the enhancement of stem cell efficacy may include an increase in expression of at least one of the following genes: EFNA1, ADAM8, ANGPTL4, ANGPTL6, CYP1B1, APOD, KDR, EREG, ADTRP, SLC7A8, ITGA11, IL1B, FLRT3, THBD, CXCL6, ITGB8, HGF, CAMK1D, LACC1, GPR68, BDKRB2, NLRC4, SCN1A, ASS1, KCNAB2, SLC6A9, CTSW, SYT12, TNFSF13B, ABCC3, and QPCT.

In an embodiment, the enhancement of stem cell efficacy may include a decrease in expression of at least one of the following genes: EPHA2, ESM1, SLC7A10, HES1, VWC1, NEDD9, and IL31RA.

In an embodiment of the present invention, it was confirmed that the stem cells cultured using the culturing method according to the present invention have reduced sizes and superior differentiation potency, migration ability and proliferation ability compared to stem cells cultured using other culturing methods, and thus enhancement of stem cell efficacy was confirmed. In addition, increases in expression of the genes such as EFNA1, ADAM8, ANGPTL4, ANGPTL6, CYP1B1, APOD, KDR, EREG, ADTRP, SLC7A8, ITGA11, IL1B, FLRT3, THBD, CXCL6, ITGB8, HGF, CAMK1D, LACC1, GPR68, BDKRB2, NLRC4, SCN1A, ASS1, KCNAB2, SLC6A9, CTSW, SYT12, TNFSF13B, ABCC3, and QPCT and decreases in expression of the genes such as EPHA2, ESM1, SLC7A10, HES1, WWC1, NEDD9, and IL31RA were confirmed in the stem cells cultured using the culturing method according to the present invention compared to the stem cells cultured using other culturing methods (Example 7).

Therefore, the present invention provides a method for enhancing efficacy of stem cells including a step of increasing expression of at least one gene selected from EFNA1, ADAM8, ANGPTL4, ANGPTL6, CYP1B1, APOD, KDR, EREG, ADTRP, SLC7A8, ITGA11, IL1B, FLRT3, THBD, CXCL6, ITGB8, HGF, CAMK1D, LACC1, GPR68, BDKRB2, NLRC4, SCN1A, ASS1, KCNAB2, SLC6A9, CTSW, SYT12, TNFSF13B, ABCC3, and QPCT. In addition, the present invention provides a method for enhancing efficacy of stem cells including a step of decreasing expression of at least one gene selected from EPHA2, ESM1, SLC7A10, HES1, VWVC1, NEDD9, and 1L31RA. The enhancement of stem cell efficacy is as described above.

The increase and decrease in gene expression may be achieved by using any method known in the art or by culturing stem cells using the culturing method provided by the present invention. However, the embodiment is not limited thereto.

In the present invention, the "growth factor" refers to a substance involved in division, growth, or differentiation of cells.

The growth factor of the present invention includes brain-derived neurotropic factor (BDNF), fibroblast growth factor (FGF), hepatocyte growth factor (HGF), nerve growth factor (NGF), vascular endothelial growth factor (VEGF), insulin-like growth factor (IGF), transforming growth factor (TGF), platelet-derived growth factor (PDGF), bone-derived growth factor (BDF), colony stimulation factor (CSF), epi-dermal growth factor (EGF), and keratinocyte growth factor (KGF).

In the present invention, the "proliferation" of a cell includes intracellular responses involving an increase in the number of cells, DNA replication, cell division, and increases in various cellular components. Specifically, the cell proliferation may refer to an increase in the number of cells. The cell proliferation may include cell regeneration that is the ability to generate an exact copy of itself. In an embodiment, the cell proliferation may be "undifferentiated proliferation". The undifferentiated proliferation refers to proliferation of a stem cell into cells having the same properties as those of a parent cell, i.e., cells having pluripo-tency without being differentiated into certain cells.

In the present invention, the "differentiation" refers to a phenomenon in which the structure or function of a cell is specialized. That is, differentiation is a process in which morphology and function of cells or tissues of organisms are changed into suitable forms for performing tasks individu-ally provided thereto. For example, a process of changing pluripotent stem cells such as embryonic stem cells into ectoderm cells, mesoderm cells, and endoderm cells is included in differentiation. In the present invention, the "improvement in differentiation potency" also includes an improvement in the ability to differentiate into cells of a particular tissue, when needed.

In the present invention, the "immunoregulatory ability" refers to the ability to suppress or activate an immune response in a living organism and includes an action that suppresses an immune response accelerated in the living organism, revives and enhances a declined immune response, and does not affect a normal immune response. The immunoregulatory ability may involve an increase or decrease in expression of cytokines and an increase or suppression of immunoregulatory cells, without being lim-ited thereto. The immunoregulatory ability may be con-nected to treatment of immunological diseases and inflam-matory diseases, but is not limited thereto.

In the present invention, the "migration ability" may refer to an effect on enhancing migration activity of stem cells. Specifically, the enhancement of migration ability include all of the effects on increasing the migration ability of stem cells from a transplant site to an injured site, increasing the migration ability of stem cells from bone marrow to periph-eral blood, and increasing the migration ability of stem cells from peripheral blood to a specific tissue or organ such as lymph nodes, heart, lungs, liver, skin, spleens, small and large intestines, stomach, pancreas, or the like. The enhanced migration ability of stem cells from the transplant site to the injured site leads to effects such as a reduction in the number of effective stem cells for transplantation, a decrease in the in vitro culture period of stem cells thereby, enhancement of safety of stem cells, thereby including the aforementioned effects. In addition, the accelerated migra-tion of stem cells from bone marrow to peripheral blood may facilitate separation of a large number of the migrated stem cells from the peripheral blood, thereby facilitating collec-tion of stem cells for transplantation of bone marrow-derived stem cells. Also, the accelerated migration of stem cells from the peripheral blood to a peripheral organ may improve therapeutic effects on a disease, thereby including the aforementioned effects.

As used herein, the term "engraftment capacity" refers to the ability of cells differentiated from the transplanted stem cells, cells generated in vivo after transplantation, or injected cells to replace lost or injured cells. Enhancement of the engraftment capacity leads to effects such as a reduction in the number of effective stem cells for transplantation, a decrease in the in vitro culture period of stem cells thereby, and enhancement of safety of stem cells, thereby including the aforementioned effects.

As used herein, the term "bio-nanoparticle" refers to a cell-derived substance that is produced by an intracellular or extracellular stimulus and secreted through a cell membrane. The bio-nanoparticles may be classified into exosomes, microparticles, shedding vesicles, and microvesicles based on size thereof. The bio-nanoparticles may include a cell-derived substance, such as a growth factor, without being limited thereto.

As used herein, the term "angiogenic potential" refers to the ability of stem cells to form new blood vessels from pre-existing blood vessels and means the capability of growing a vascular system via processes of sprouting and splitting. The angiogenic potential of stem cells is closely related to formation, growth, and development of tissue and wound healing. As a method of evaluating the angiogenic potential of stem cells, tube formation assay may be used. The tube formation assay may be performed by any method known in the art (J Vis Exp. 2014; (91): 51312. et al).

In the present invention, regulation of expression of a factor involved in a signaling pathway includes a change in expression of a factor contributing to activation or inacti-vation of the signaling pathway capable of enhancing effi-cacy of stem cells. In an embodiment, expression of the factor involved in a signaling pathway may be regulated by inducing activation of a signaling pathway that induces a decrease in size of stem cells.

In an example embodiment, the factor involved in a signaling pathway may be selected from PI3K, Akt, PTEN, mTOR, STAT, MAPK, MEK, Raf, Ras, SOS, Grb-2, ERK, IGF, IGF-1R, IRS, Pten, TSC, Bcl-2, eIF4G, mTORC2, Bax, RP-S6, P-S6K1, 4E-BP1, Rheb, p53, Gsk, and Caspase, but is not limited thereto, and any factor involved in the IGF pathway, the PI3K pathway, the AKT pathway, the mTORC1 pathway, or the IGF/PI3K/AKT/mTORC1 pathway may be included without limitation. As another example embodiment, any factor involved in the Wnt signaling, the Inflammatory Response Pathway, the Integrin signaling pathway, the Interferon (IFN) signaling pathway, the JAK-STAT signaling pathway, the Erk signaling pathway, the MAPK Cell Signaling Pathway, the Toll-like Receptor (TLR) signaling pathway, and the like may also be included in the scope of the present invention. As another example embodiment, BDNF, FGF, HGF, NGF, VEGF, TGF, PDGF, BDF, CSF, EGF, KGF and any factor involved in pathways regulated by these factors may be included in the scope of the present invention.

However, the embodiment is not limited to the above-described signaling pathways, and regulation of expression of any other signaling pathways capable of inducing a decrease in size of stem cells and factors involved therein may be included herein without limitation.

The "stem cell" of the present invention is a cell capable of differentiating into various tissues, i.e., an undifferentiated cell. The stem cells may be pluripotent stem cells, adult stem cells, induced pluripotent stem cells, or embryonic stem cells.

The stem cells which may be human- or animal-derived stem cells may be derived from umbilical cord, umbilical cord blood, bone marrow, fat, muscle, nerve, skin, amnion, or placenta, but are not limited thereto.

The stem cells of the present invention may be, specifically, adult stem cells. The adult stem cells are undifferentiated cells that differentiate into cells of a specific tissue if required and may be extracted from grown body tissue such as bone marrow or brain cells. The adult stem cells may include at least one selected from the group consisting of mesenchymal stem cells, human tissue-derived mesenchymal stromal cells, human tissue-derived mesenchymal stem cells, and multipotency stem cells. However, the embodiment is not limited thereto.

Another aspect of the present invention provides a cell therapy product including stem cells cultured in a membrane coated with fibronectin as an active ingredient.

Another aspect of the present invention provides a composition for preventing or treating a disease including stem cells cultured in a membrane coated with fibronectin; a culture broth thereof; and at least one of the stem cells and a substance derived from the culture broth, as an active ingredient.

Another aspect of the present invention provides a method for producing a cell therapy product, the method including obtaining stem cells having enhanced efficacy by culturing the stem cells in a membrane coated with fibronectin.

Another aspect of the present invention provides a method for treating a disease, the method including administering the cell therapy product into a subject.

The disease may include any disease without limitation, as long as occurrence of the disease may be suppressed or delayed or symptoms thereof may be alleviated or ameliorated by administering the stem cells, a culture thereof, and a substance derived therefrom. For example, the disease includes diseases caused by loss of cells constituting a specific tissue and damage to the tissue caused thereby.

In the present invention, the "cell therapy product", which refers to a pharmaceutical manufacturing using cells and tissues prepared by isolation from an individual, culture, and specific manipulation and used for the purpose of treatment, diagnosis, and prevention of a disease (FDA regulations, USA), means a pharmaceutical used for the purpose of treatment, diagnosis, and prevention of a disease through a series of actions such as proliferation and selection of living autologous, allogenic, or xenogenic cells in vitro or changes of biological properties of the cells by different methods, in order to restore the functions of cells or tissues.

The cell therapy product of the present invention may include $1.0 \times 10$ cells/ml to $1.0 \times 10^9$ cells/ml, without being limited thereto. The cell therapy product of the present invention may be used as in a non-frozen state or can be frozen for the next use. To freeze the cell therapy product, a standard cryopreservative (ex: DMSO, glycerol, or Epilife™ cell freezing medium (Cascade Biologics)) is added to the population of cells before the cells are frozen. In addition, the cell therapy product may be administered after being formulated into a unit administration formulation suitable for administration into a patient's body according to a common method in the pharmaceutical field, and the formulation may include an administration dose which is effective after administration once or several times. As formulations proper for such a purpose, injection agents such as injectable ampoules, injecting agents such as injection bags, and sprays such as aerosol formulations may be used. The injectable ampoules may be prepared in a mixed state with injection liquids immediately before use, and as injection liquids, physiological saline solution, glucose, mannitol, Ringer's solution, etc. may be used. In addition, the injection bags may be made of polyvinyl chloride or polyethylene, and injection bags of Baxter, Becton-Dickinson, Medcep, National Hospital Products, or Terumo may be used.

The cell therapy product may further include at least one pharmaceutically acceptable common inert carrier, e.g., a preservative, an analgesic, a solubilizer, and a stabilizer for injectable formulations, and a base, an excipient, a lubricant, or a preservative for topical formulations.

The cell therapy product of the present invention prepared as described above may be administered by any administration method commonly used in the art along with other stem cells, which are used for transplantation and other uses, or in a mixed form with these stem cells, and may be directly engrafted or transplanted to the disease area or directly transplanted or infused to the abdominal cavity of a patient in need of treatment, but is not limited thereto. Furthermore, the administration may be performed either by non-surgical administration using a catheter or by surgical administration via injection into or transplantation to a disease area after excising the disease area. In addition to parenteral administration according to a common method, for example, direct administration into a lesion, transplantation by infusion into the blood vessel, which is a general method for hemopoietic stem cell transplantation, is also possible.

The cell therapy product may be administered once or as several divided doses. However, it should be understood that the actual dose of active ingredients is determined in consideration of various related factors, such as a disease to be treated, severity of the disease, administration route, a patient's body weight, age, and gender, etc., and thus the administration dose should not be construed as limiting the scope of the present invention in any manner.

The cell therapy product of the present invention may be used to regenerate or protect adipocytes, osteocytes, chondrocytes, muscle cells, nerve cells, cardiomyocytes, hepatocytes, pancreatic islet beta cells, vascular cells, or lung cells. Specifically, the cell therapy product of the present invention may be used to regenerate or protect adipocytes, osteocytes, or chondrocytes.

Therefore, another aspect of the present invention provides a composition for treating a bone disease or a cartilage disease including stem cells cultured in a membrane coated with fibronectin; a culture broth thereof; or at least one of the stem cells and a substance derived from the culture broth, as an active ingredient, and another aspect of the present invention provides a method for treating a bone disease or a cartilage disease, the method including administering the composition to a subject.

As used herein, the term "bone disease" including all diseases that may be caused by a decrease in bone density may be a disease caused by deformation or loss of bone cells or bone tissues, specifically, may include osteoporosis, rheumatoid arthritis, periodontal disease, osteomalacia, osteogenesis imperfecta, osteopetrosis, osteosclerosis, Paget's disease, adynamic bone disease, metabolic bone disease, rickets, and the like, without being limited thereto.

As used herein, the term "cartilage disease", also referred to as "cartilage damage disease", means a disease caused when cartilage, cartilage tissue, and/or articular tissue (e.g., synovial membrane, articular capsule, and subchondral bone) are damaged by a mechanical stimulus or inflammatory response. The cartilage disease may be a disease caused by deformation or loss of chondrocytes or cartilage tissue, specifically, degenerative arthritis, rheumatoid arthritis, fracture, damage to muscle tissue, plantar fasciitis, tennis elbow, calcific myositis, fracture nonunion, or articular damage caused by external injury, but is not limited thereto.

In addition, the cell therapy product of the present invention is characterized in that it is effective on one selected from the group consisting of: treatment of a lung disease; inhibition or treatment of inflammation caused by a lung disease; regeneration of lung tissue; and inhibition of pulmonary fibrosis, and the cell therapy product may inhibit or alleviate inflammatory response and fibrosis caused by a lung disease. Furthermore, the cell therapy product of the present invention may be used to treat a cardiovascular disease or regenerate cartilage. Also, the cell therapy product of the present invention may enhance immunoregulatory function or deteriorate immunifacient, Immune cell infiltration, or immunogenicity and may suppress an inflammatory response, and therefore the cell therapy product may be used for treatment thereof, without being limited thereto.

Mode for Invention

Hereinafter, the present invention will be described in more detail with reference to the following examples and experimental examples. However, the following examples and experimental examples are merely presented to exemplify the present invention, and the scope of the present invention is not limited thereto.

Example 1

Analysis of Shape of Umbilical Cord Blood-derived Mesenchymal Stem Cells in Attached State Umbilical cord blood-derived mesenchymal stem cells were equally inoculated onto a 6-well plate; and a 6-well plate coated with a fibronectin-coated PVDF membrane in the form of film formed by electrospinning (hereinafter, referred to as membrane), respectively, at a density of $1\times10^5$ cells/well and cultured in a 5% $CO_2$ incubator at 37° C. for 48 hours. Subsequently, the cells were washed with PBS and immobilized using 3% glutaraldehyde. Then, the cells were dehydrated by sequentially treating with 60%, 70%, 80%, 90%, and 100% ethanol and completely dried, and SEM images were obtained at a magnification of 2000×. As a result, it is confirmed that the 3D structures of the stem cells are relatively maintained when cultured in the membrane compared to the stem cells cultured in the common plate (FIG. 1).

Example 2

Figure 2:
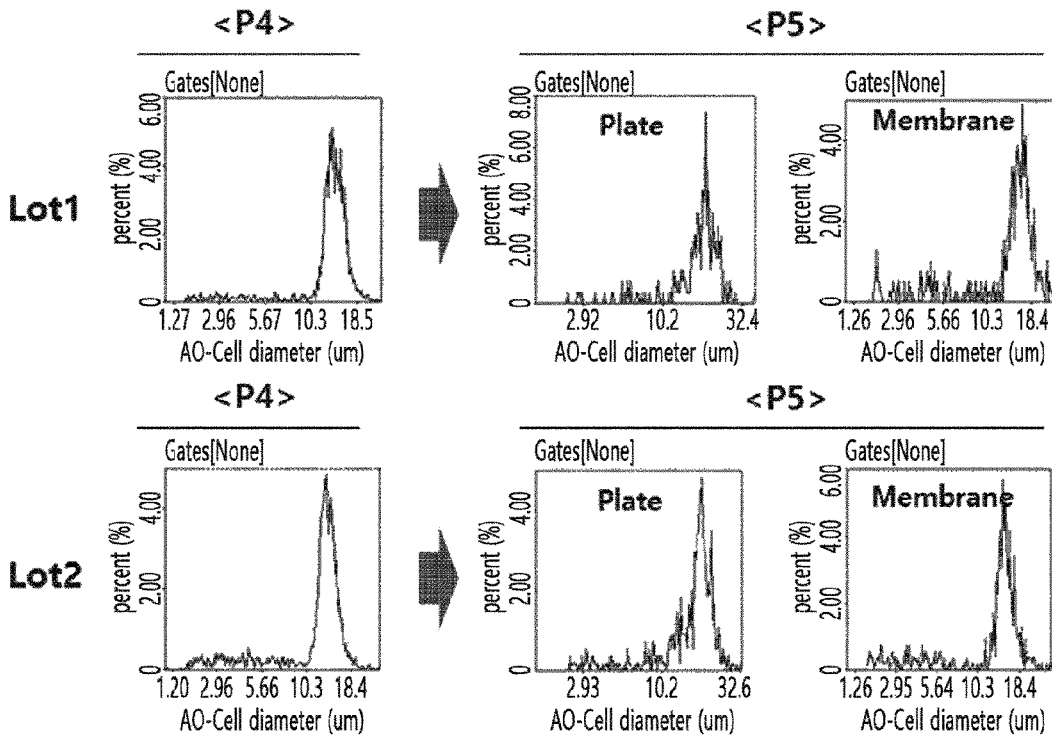
FIG. 2 shows sizes of umbilical cord blood-derived mesenchymal stem cells in an unattached state according to culturing conditions.

Analysis of Size of Umbilical Cord Blood-derived Mesenchymal Stem Cells in Unattached State The umbilical cord blood-derived mesenchymal stem cells cultured under the common culturing conditions and the membrane culturing conditions according to Example 1 were treated with a TrypLE reagent to obtain single cells. Then, sizes of the obtained single cells were comparatively analyzed using an NC200 device. As a result, it is confirmed that diameters of the stem cells cultured in the membrane are smaller than those of the mesenchymal stem cells cultured in the common plate (FIG. 2).

Example 3

Figure 3:
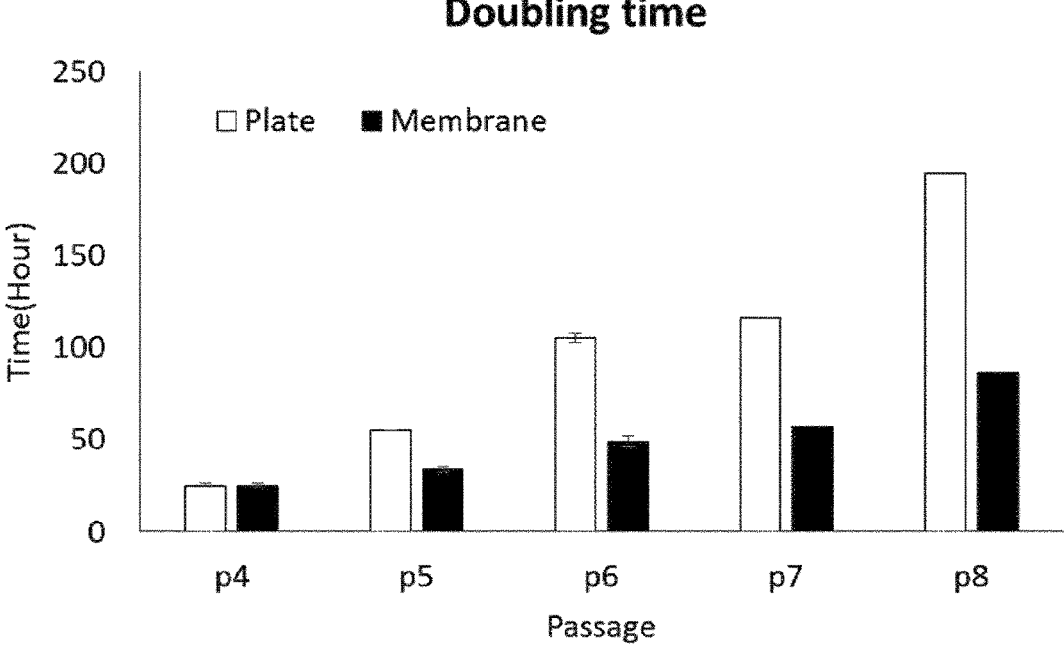
FIG. 3 shows proliferation ability of umbilical cord blood-derived mesenchymal stem cells according to culturing conditions.

Comparison of Proliferation Ability of Umbilical Cord Blood-derived Mesenchymal Stem Cells According to Culturing Conditions For a comparative analysis of the proliferation ability of umbilical cord blood-derived mesenchymal stem cells according to culturing conditions, the umbilical cord blood-derived mesenchymal stem cells were equally inoculated onto a common 6-well plate and a membrane-coated 6-well plate at a density of $1\times10^5$ cells/well and cultured in a 5% $CO_2$ incubator at 37° C. from P4 to P8 under respective culturing conditions. In order to measure cell division time, the following expression was used $(T-T_0)\log 2/\log N-\log N_0$, (T: final time (h), To: initial time (h), N: final cell number, and $N_0$: initial cell number). As a result, it is confirmed that the division time of the mesenchymal stem cells serially subcultured in the membrane significantly decreases compared to the division time of the mesenchymal stem cells serially subcultured in the common plate (FIG. 3).

Example 4

Analysis of Differentiation Potency of Umbilical Cord Blood-derived Mesenchymal Stem Cells According to Culturing Conditions For a comparative analysis of differentiation potency, potencies of osteogenic differentiation, adipogenic differentiation, and chondrogenic differentiation were comparatively analyzed under common culturing conditions and membrane culturing conditions.

4-1. Induction and Analysis of Osteogenic Differentiation

For induction of osteogenic differentiation, $5\times10^4$ stem cells were inoculated onto a 6-well plate and a membrane-coated 6-well plate, respectively, and cultured in a 5% $CO_2$ incubator at 37° C. for one day, and the culture medium was replaced with an osteogenic differentiation culture medium (Stempro). Differentiation was induced for 2 weeks while replacing the differentiation culture medium at every 2 to 3 days. The differentiated cells were washed twice with PBS and immobilized by adding 2 ml of 4% paraformaldehyde to each well at room temperature for 10 minutes. Subsequently, the cells were washed twice with PBS and stained by adding 2 mL of a 2% Alizarin Red S reagent to each well and incubating at room temperature for 15 minutes. After removing the staining reagent, the cells were washed twice with triple distilled water and examined using a microscope.

In order to perform a comparative analysis of expression of osteogenic differentiation-related factors in mRNA levels, total RNAs were obtained from the cells after osteogenic differentiation and cDNAs were synthesized respectively therefrom using an RT-Premix (Biorad). Expressions of Osteocalcin (OCN) and Osterix were compared with each other in the mRNA levels by performing PCR using the synthesized cDNAs as templates and the following primers. In this case, GAPDH was used as an internal control.

OCN F: 5'-AGC AAA GGT GCA GCC TTT GT-3' (SEQ ID NO: 1)
OCN R: 5'-GCG CCT GGG TCT CTT CAC T-3' (SEQ ID NO: 2)
Osterix F: 5'-TGG CCA TGC TGA CTG CAG CC-3' (SEQ ID NO: 3)
Osterix R: 5'-TGG GTA GGC GTC CCC CAT GG-3' (SEQ ID NO: 4)

Figure 4A:
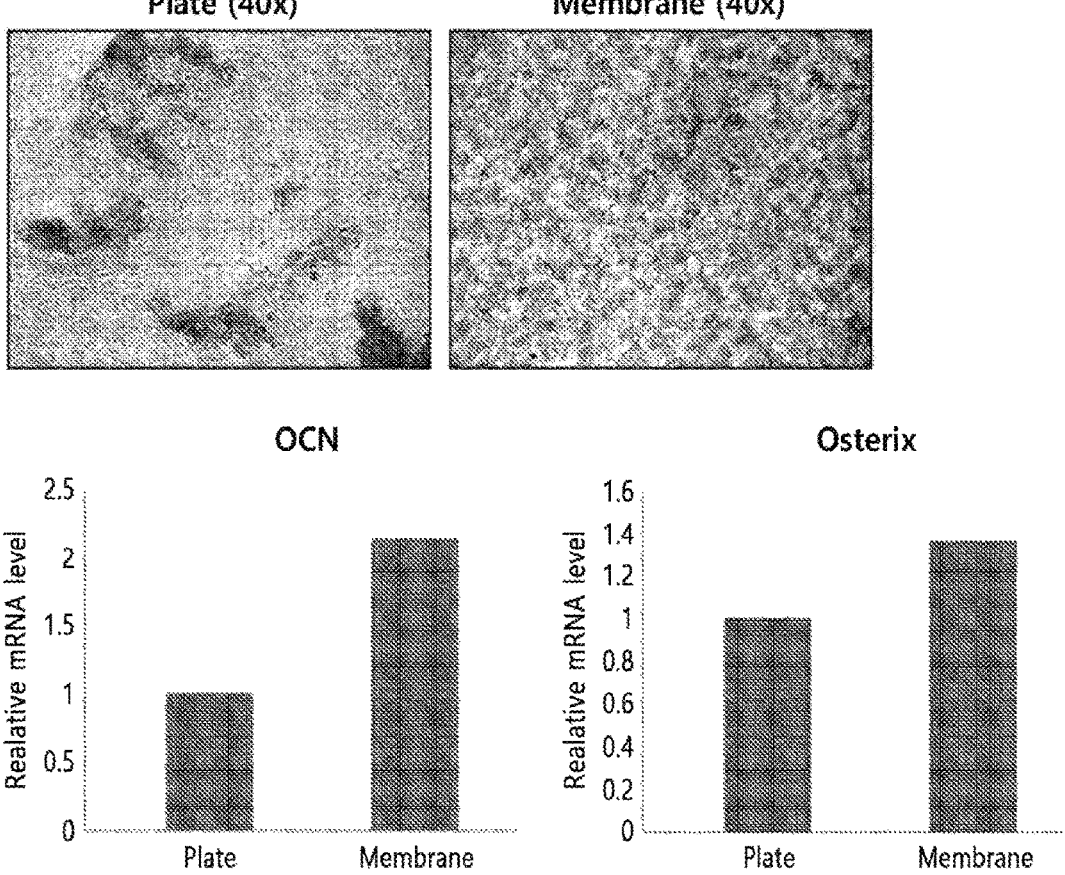
FIGS. 4A-C show results of a comparative analysis of differentiation potency of umbilical cord blood-derived mesenchymal stem cells according to culturing conditions.

As a result, it is confirmed that osteogenic differentiation potency increases in the mesenchymal stem cells cultured in the membrane compared to those cultured in the common plate (FIG. 4a).

4-2. Induction and Analysis of Adipogenic Differentiation

For induction of adipogenic differentiation, $1 \times 10^5$ stem cells were inoculated onto a 6-well plate and a membrane-coated 6-well plate, respectively, and cultured in a 5% $CO_2$ incubator at 37° C. for one day, and the culture medium was replaced with an adipogenic differentiation culture medium (Stempro). Differentiation was induced for 2 weeks while replacing the differentiation culture medium at every 2 to 3 days. The differentiated cells were washed twice with PBS and immobilized by adding 2 ml of 4% paraformaldehyde to each well at room temperature for 10 minutes. Subsequently, the cells were washed twice with triple distilled water and washed once with 60% isopropanol, and stained by adding 2 mL of an Oil red O reagent to each well and incubating at room temperature for 30 minutes. After removing the Oil red O reagent staining reagent, the cells were washed twice with triple distilled water and examined using a microscope.

In order to perform a comparative analysis of expression of adipogenic differentiation-related factors in mRNA levels, total RNAs were obtained from the cells after adipogenic differentiation and cDNAs were synthesized respectively therefrom using an RT-Premix (Biorad). Expressions of peroxisome proliferator-activated receptor gamma (PPARγ) and lipoprotein lipase (LPL) were compared with each other in the mRNA levels by performing PCR using the synthesized cDNAs as templates and the following primers. In this case, GAPDH was used as an internal control.

PPARγ F: 5'-CAG GAA AGA CAA CAG ACA AAT CA-3' (SEQ ID NO: 5)
PPARγ R: 5'-GGG GTG ATG TGT TTG AAC TTG-3' (SEQ ID NO: 6)
LPL F: 5'-AGA CAC AGC TGA GGA CAC TT-3' (SEQ ID NO: 7)
LPL R: 5'-GCA CCC AAC TCT CAT ACA TT-3' (SEQ ID NO: 8)

Figure 4B:
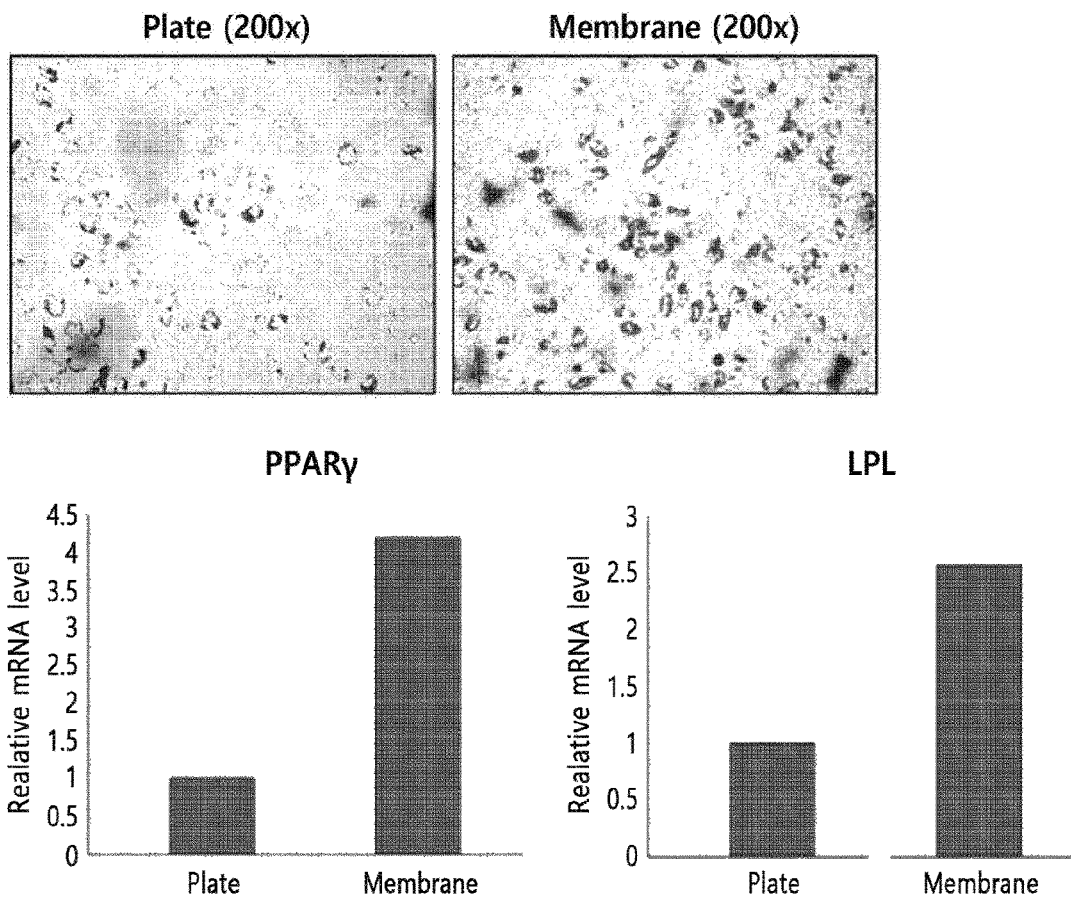

As a result, it is confirmed that adipogenic differentiation potency increases in the mesenchymal stem cells cultured in the membrane compared to those cultured in the common plate (FIG. 4b).

4-3. Induction and Analysis of Chondrogenic Differentiation

For induction of chondrogenic differentiation, cells were induced formation of $1 \times 10^5/10$ μL of micromass at a 6-well plate and a membrane-coated 6-well plate. After culturing the cells in a 5% $CO_2$ incubator at 37° C. for about 4 hours and confirming stable formation of the micromass, a chondrogenic differentiation culture medium (Stempro) was added thereto. Differentiation was induced for 10 days while replacing the differentiation culture medium at every 2 to 3 days. The differentiated micromass was washed twice with PBS and immobilized by adding 2 ml of 4% paraformaldehyde to each well at room temperature for 10 minutes. Subsequently, the cells were stained with a 1% Alcian blue (in 3% acetic acid) reagent for 30 minutes and examined using a microscope.

In order to perform a comparative analysis of expression of chondrogenic differentiation-related factors in mRNA levels, total RNAs were obtained from the cells after chondrogenic differentiation and cDNAs were synthesized respectively therefrom using an RT-Premix (Biorad). Expressions of collagen type 2 (Col2) and aggrecan were compared with each other in the mRNA levels by performing PCR using the synthesized cDNAs as templates and the following primers. In this case, GAPDH was used as an internal control.

Col2 F: 5'-CGT CCA GAT GAC CTT CCT ACG-3' (SEQ ID NO: 9)
Col2 R: 5'-TGA GCA GGG CCT TCT TGA G-3' (SEQ ID NO: 10)
Aggrecan F: 5'-CTG CAT TCC ACG AAG CTA ACC T-3' (SEQ ID NO: 11)
Aggrecan R: 5'-GAC GCC TCG CCT TCT TGA A-3' (SEQ ID NO: 12)

Figure 4C:
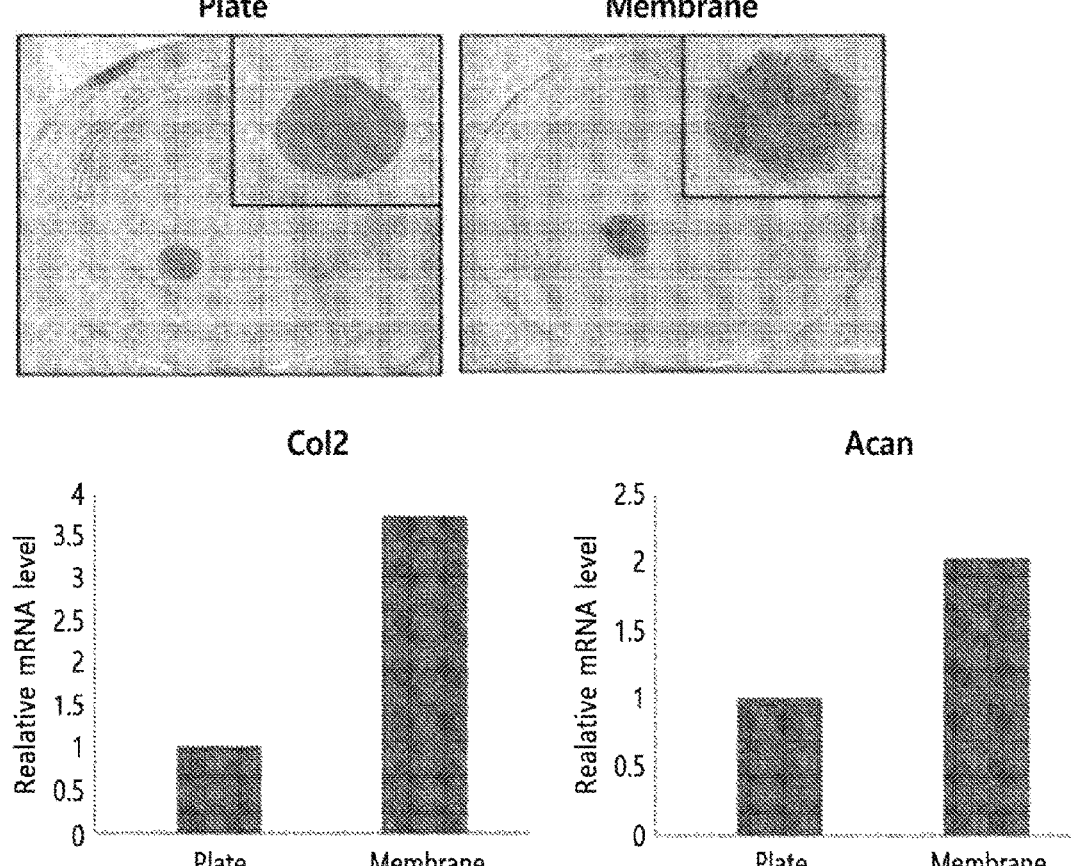

As a result, it is confirmed that chondrogenic differentiation potency increases in the mesenchymal stem cells cultured in the membrane compared to those cultured in the common plate (FIG. 4c).

Example 5

Comparative Analysis of Cell Migration Ability According to Culturing Conditions For a comparative analysis of migration ability of umbilical cord blood-derived mesenchymal stem cells according to culturing conditions, Boyden chamber assay was used. $5 \times 10^5$ umbilical cord blood-derived mesenchymal stem cells were inoculated onto a common 100 mm dish and a membrane-coated 100 mm dish, respectively, and cultured in a 5% $CO_2$ incubator at 37° C. On the 4th day of culture, the medium was replaced with an FBS-free medium and the cells were additionally cultured for one day. Among the subcultured cells after culturing, $5 \times 10^4$ cells were loaded in an upper chamber of the Boyden chamber and a culture medium containing 10% FBS was loaded in a lower chamber, and then migration of the cells was induced for 18 hours. After the cell migration, the upper chamber was stained with a Crystal violet reagent and the cells on the surface of the upper membrane were removed and cells migrated to the lower chamber were examined using a microscope and analyzed by detection using the staining reagent.

Figure 5:
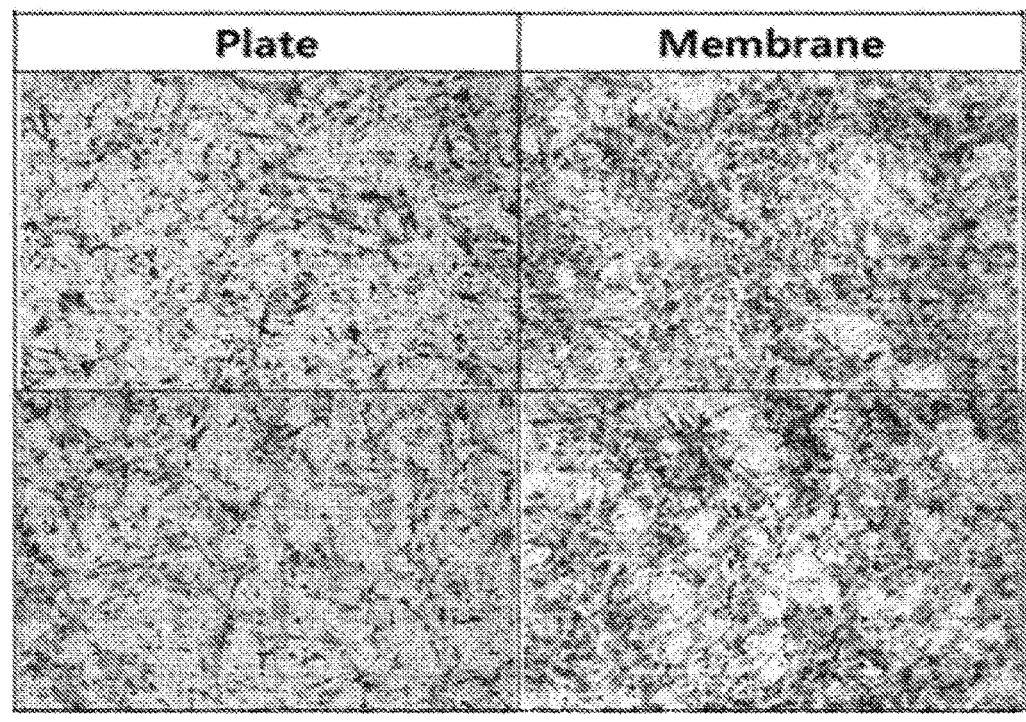
FIG. 5 shows results of a comparative analysis of cell migration ability of umbilical cord blood-derived mesenchymal stem cells according to culturing conditions.
Figure 5:
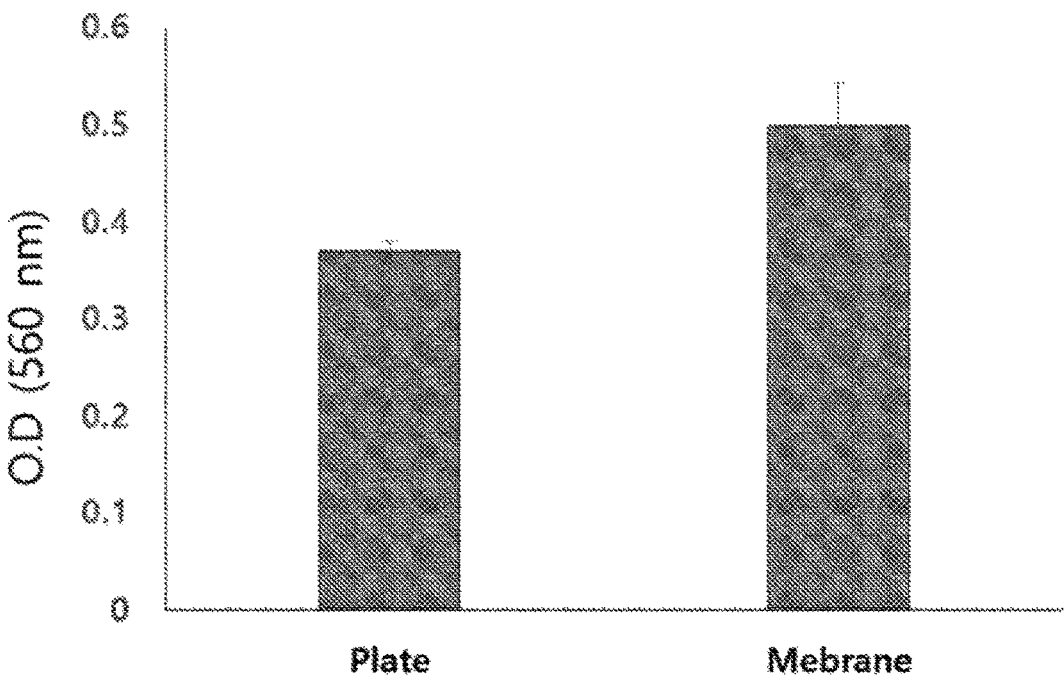

As a result, it is confirmed that the migration ability of the mesenchymal stem cells cultured in the membrane is enhanced compared to the cells cultured in the common plate (FIG. 5).

Example 6

Comparative Analysis of Angiogenic Potential According to Culturing Conditions For a comparative analysis of tube formation ability of umbilical cord blood-derived mesenchymal stem cells according to culturing conditions, $5\times10^5$ umbilical cord blood-derived mesenchymal stem cells were inoculated onto a common 100-well plate and a membrane-coated 100-well plate, respectively, and cultured in a 5% $CO_2$ incubator at 37° C. for 5 days. Among the subcultured cells after the culturing, $2\times10^4$ cells were inoculated onto a 48-well plate coated with 100 μL of Matrigel and tube formation was analyzed at every observation hour using a microscope while incubating the cells in a human umbilical vein endothelial growth medium (CEFO bio) in a $CO_2$ incubator at 37° C.

Figure 6:
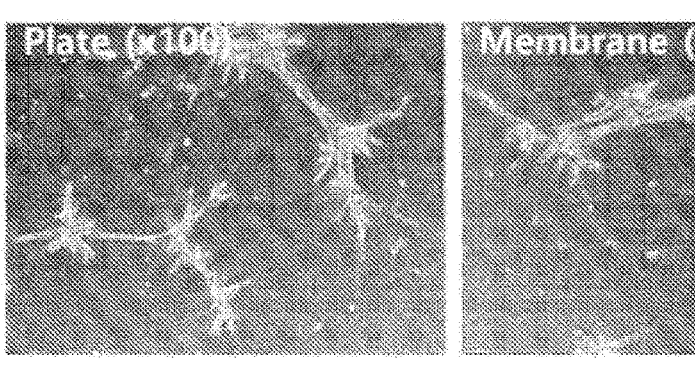
FIG. 6 shows results of a comparative analysis of tube formation ability of umbilical cord blood-derived mesenchymal stem cells according to culturing conditions.
Figure 6:
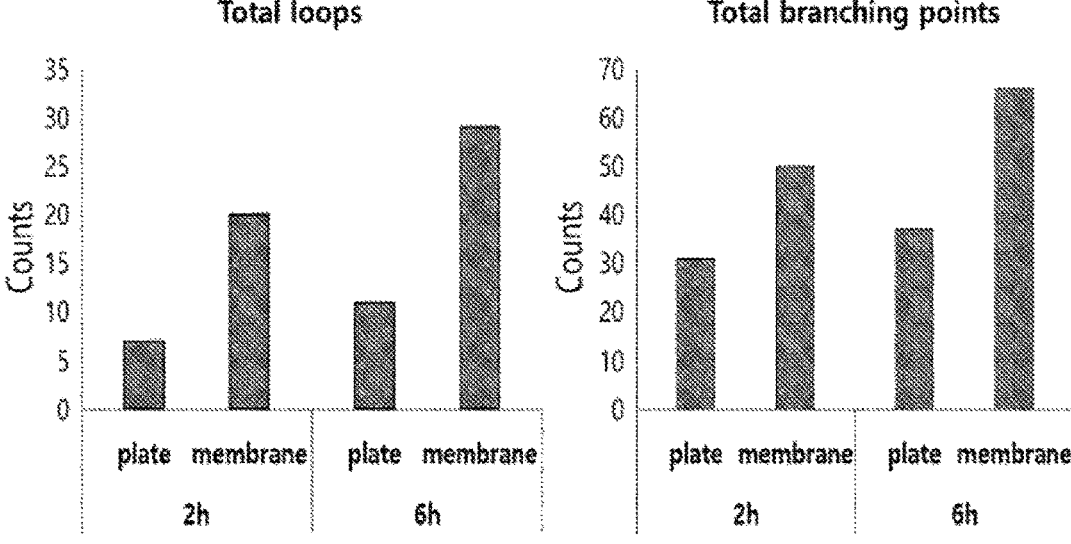

As a result, it is confirmed that the tube formation ability of the mesenchymal stem cells cultured in the membrane is enhanced compared to the cells cultured in the common plate via examination using a microscope (FIG. 6) and it is confirmed that the numbers of loops and branching points of the mesenchymal stem cells cultured in the membrane are greater than those of the cells cultured in the common plate based on results of 2-hour and 6-hour analyses (FIG. 6).

Example 7

Comparative Analysis of Gene Expression According to Culturing Conditions

Figure 7A:
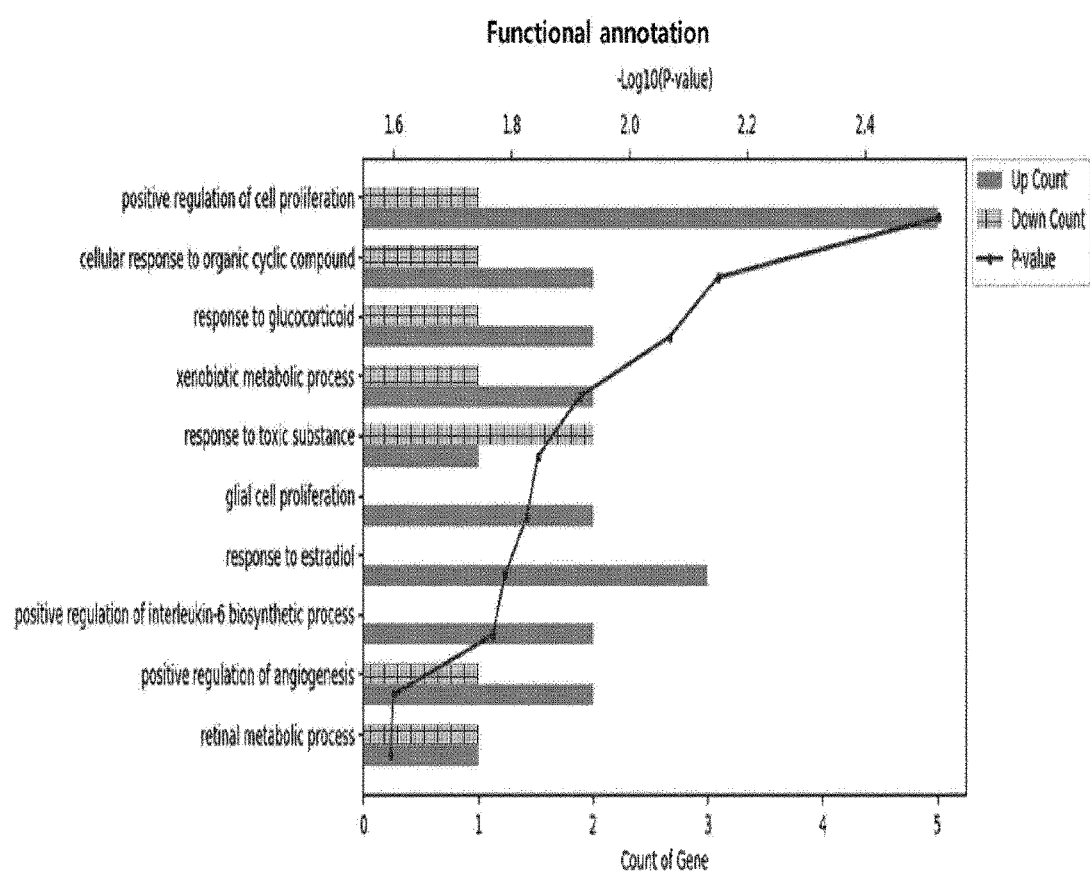
FIGS. 7A-C show results of a comparative analysis of gene expression levels of umbilical cord blood-derived mesenchymal stem cells according to culturing conditions.
Figure 7B:
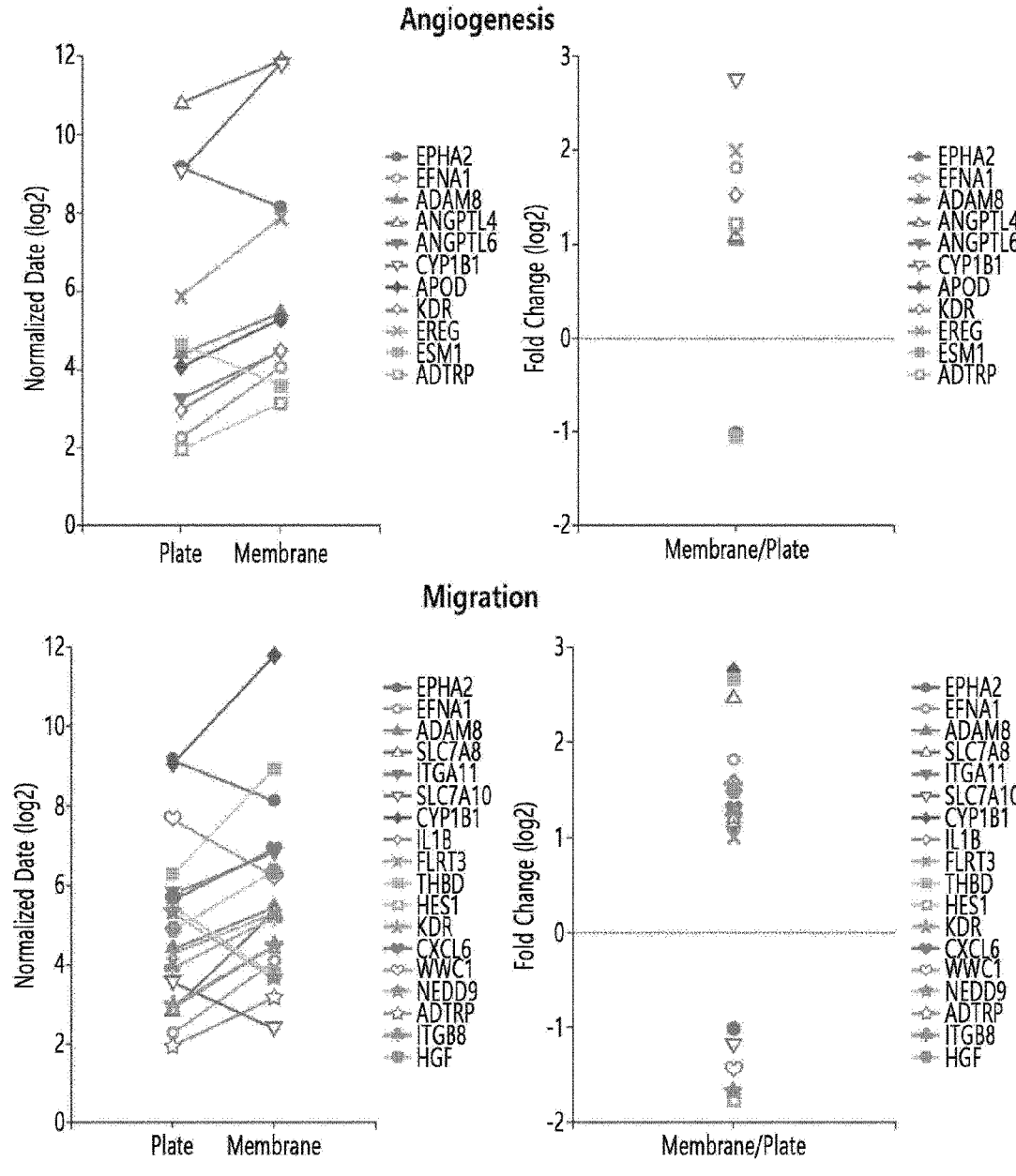
Figure 7C:
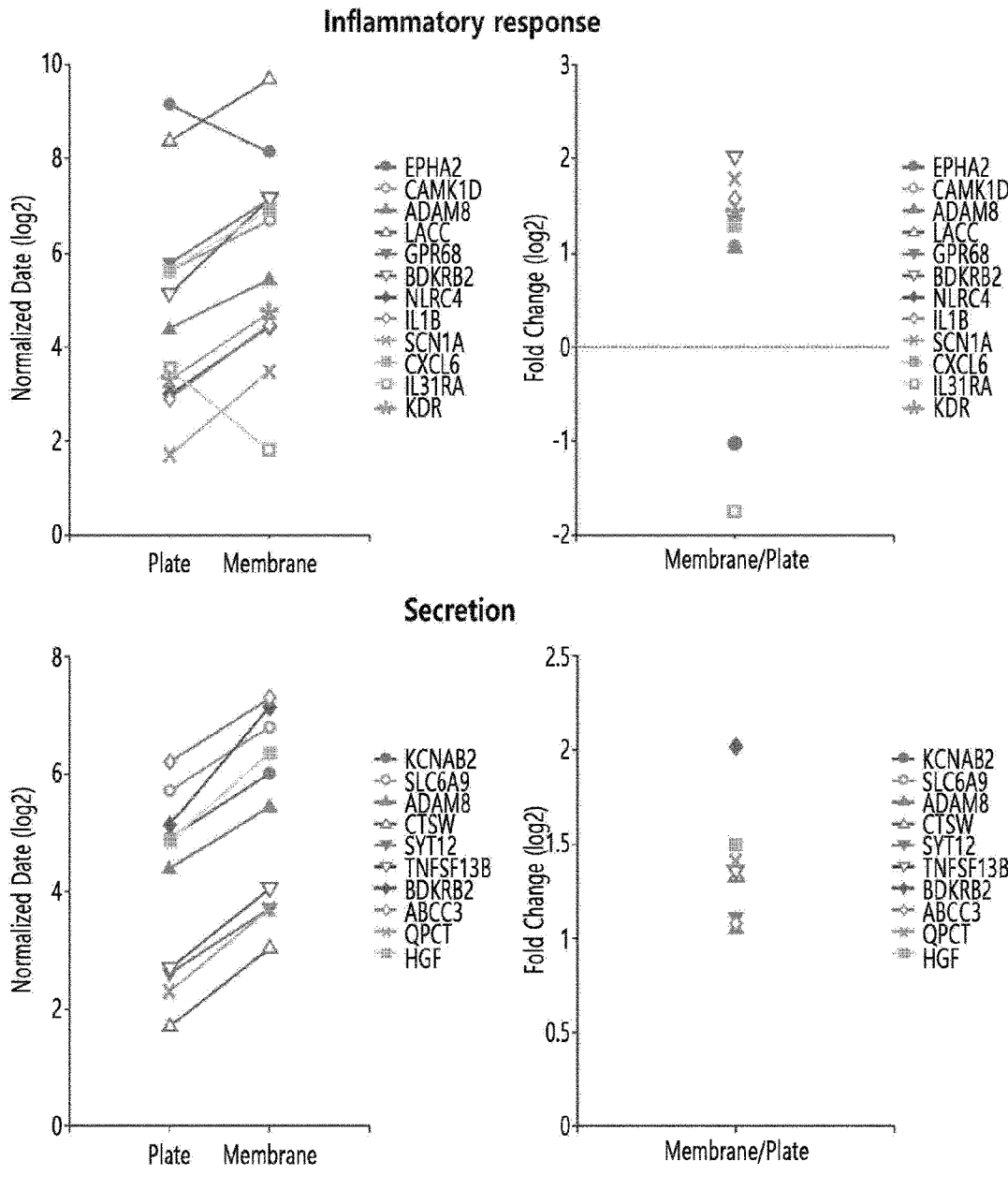

For a comparative analysis of gene expression of umbilical cord blood-derived mesenchymal stem cells according to culturing conditions, $5\times10^5$ umbilical cord blood-derived mesenchymal stem cells were inoculated onto a common 100-well plate and a membrane-coated 100-well plate, respectively, and cultured in a 5% $CO_2$ incubator at 37° C. for 3 days. For a comparative analysis in mRNA levels, total RNAs were obtained from the cells obtained in Example 7 above and functional annotation and selected gene plot analyses were conducted. As a result of the functional annotation analysis, it was confirmed that the proliferation ability of the mesenchymal stem cells cultured in the membrane was enhanced compared to the mesenchymal stem cells cultured in the common plate. As a result of the selected gene plot analysis, changes in expression of genes related to angiogenesis, migration, inflammatory response, and secretion were observed in the mesenchymal stem cells and it was confirmed that gene expression of the mesenchymal stem cells cultured in the membrane tends to increase (FIGS. 7A to 7C).

Specifically, the following changes in expression were confirmed.

TABLE 1

Changes in expression levels of angiogenesis-related genes

| Increase | Decrease |
| --- | --- |
| EFNA1 | EPHA2 |
| ADAM8 | ESM1 |
| ANGPTL4 | |

TABLE 1-continued

Changes in expression levels of angiogenesis-related genes

| Increase | Decrease |
| --- | --- |
| ANGPTL6 | |
| CYP1B1 | |
| APOD | |
| KDR | |
| EREG | |
| ADTRP | |

TABLE 2

Changes in expression levels of migration-related genes

| Increase | Decrease |
| --- | --- |
| EFNA1 | EPHA2 |
| ADAM8 | SLC7A10 |
| SLC7A8 | HES1 |
| ITGA11 | WWC1 |
| CYP1B1 | NEDD9 |
| IL1B | |
| FLRT3 | |
| THBD | |
| KDR | |
| CXCL6 | |
| ADTRP | |
| ITGB8 | |
| HGF | |

TABLE 3

Changes in expression levels of inflammatory response-related genes

| Increase | Decrease |
| --- | --- |
| CAMK1D | EPHA2 |
| ADAM8 | IL31RA |
| LACC1 | |
| GPR68 | |
| BDKRB2 | |
| NLRC4 | |
| IL1B | |
| SCN1A | |
| CXCL6 | |
| ASS1 | |

TABLE 4

Changes in expression levels of secretion-related genes
Increase

| KCNAB2 |
| --- |
| SLC6A9 |
| ADAM8 |
| CTSW |
| SYT12 |
| TNFSF13B |
| BDKRB2 |
| ABCC3 |
| QPCT |
| HGF |

Example 8

Figure 8A:
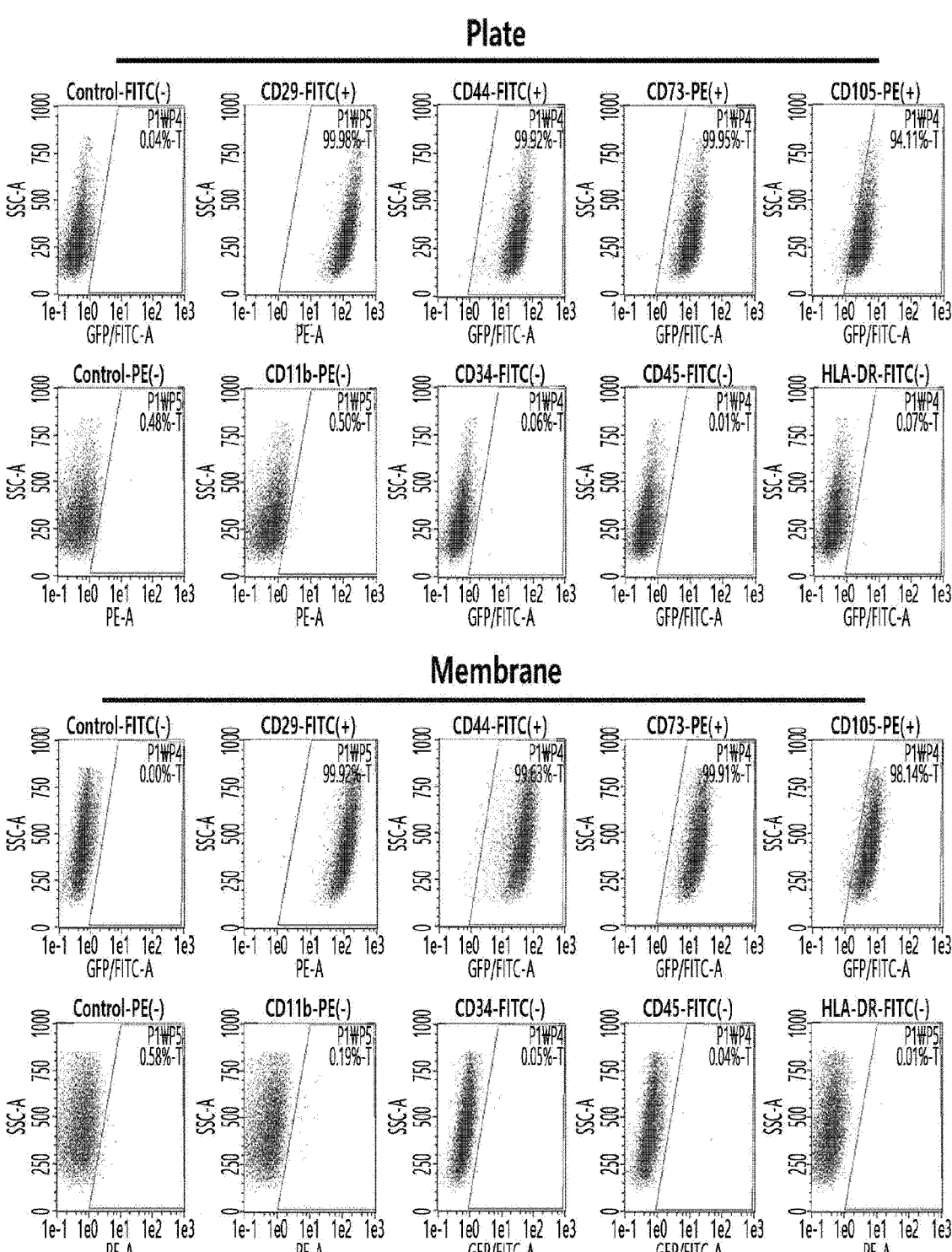
FIGS. 8A-B show results of a comparative analysis of immunophenotypes of umbilical cord blood-derived mesenchymal stem cells according to culturing conditions.
Figure 8B:
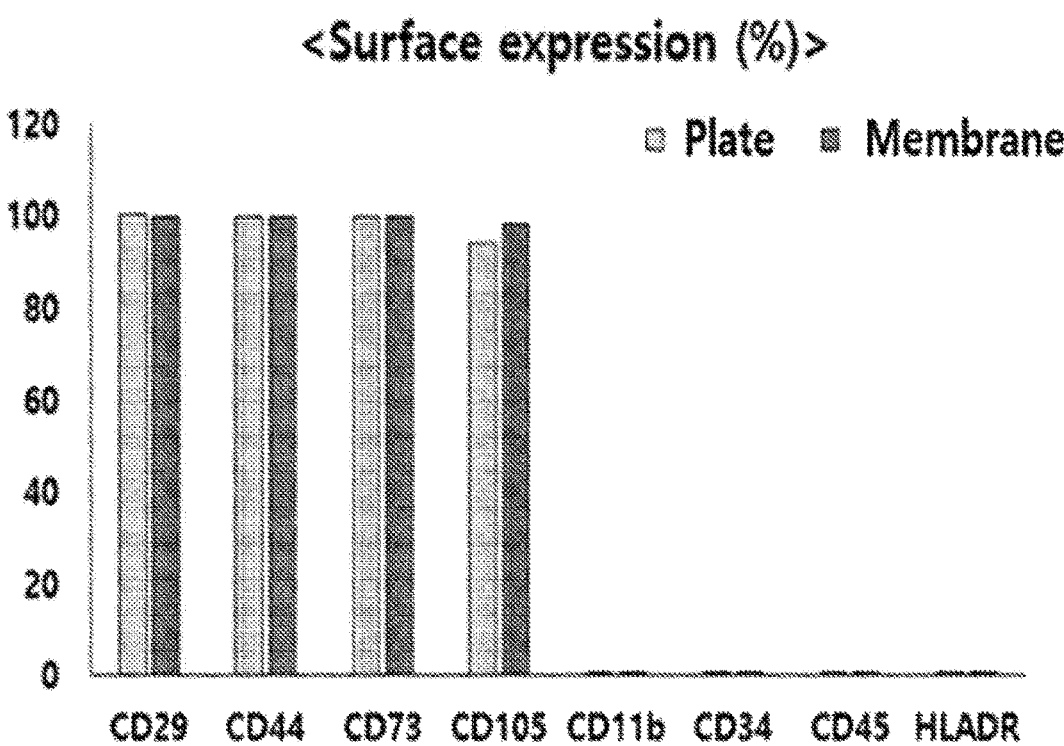

Comparative Analysis of Immunophenotypes of
Umbilical Cord Blood-derived Mesenchymal Stem
Cells According to Culturing Conditions Marker proteins (positive antigens: CD29, CD44, CD73, and CD105, and negative antigens: CD11b, CD34, CD45, and HLA-DR) were analyzed using an FACS device. The umbilical cord blood-derived mesenchymal stem cells which were cultured under the common culturing conditions and in the membrane-coated plate obtained in Example 7 above were washed with PBS and subjected to antibody reaction at room temperature. After the reaction, the cells were washed with PBS again to prepare a suspension for analysis and signals of the antibodies were detected using the FACS device (MACSQuant VYB flow cytometry analyzer) to obtain a percentage of cells expressing the marker among the total cells. Analysis was performed using MACSQuantify software. As a result, it was confirmed that no difference was observed in the positive antigens and the negative antigens between the mesenchymal stem cells cultured in the common plate and those cultured in the membrane (FIGS. 8*a* to 8*b*).

Based thereon, it was confirmed that the immunophenotypes of the stem cells were maintained in the case of using the culturing method of the present invention.

The above description of the present invention is provided for the purpose of illustration, and it would be understood by those skilled in the art that various changes and modifications may be made without changing technical conception and essential features of the present invention. Thus, it is clear that the above-described embodiments are illustrative in all aspects and do not limit the present invention. Therefore, the scope of the disclosure is defined not by the detailed description, but by the claims and their equivalents, and all variations within the scope of the claims and their equivalents are to be construed as being included in the disclosure.

The invention claimed is:

1. A method for enhancing efficacy of an umbilical cord blood-derived mesenchymal stem cell, the method comprising culturing the umbilical cord blood-derived mesenchymal stem cell on a poly(vinylidene fluoride) (PVDF) membrane in the form of a film formed by electrospinning, the PVDF membrane having a surface coated with fibronectin, wherein enhancing efficacy of a stem cell includes at least one of increase in growth factor expression, regulation of expression of a factor involved in a signaling pathway, a reduction in size of stem cells, improvement in proliferation ability, improvement in differentiation potency, improvement in immunoregulatory ability, improvement in migration ability, improvement in engraftment capacity, improvement in angiogenic potential, increase in secretion of bio-nanoparticles, decrease in immunogenicity, increase in stemness, suppression of cell viability reduction, and decrease in cellular senescence, wherein the enhancement of efficacy of the stem cell comprises:

(a) an increase in expression of at least one of EFNA1 (Ephrin-A1), ADAM8 (ADAM metallopeptidase domain 8), ANGPTL4 (Angiopoietin-like 4), ANGPTL6 (Angiopoietin-like 6), CYP1B1 (Cytochrome P450 family 1 subfamily B member 1), APOD (Apolipoprotein D), KDR (Kinase insert domain receptor), EREG (Epiregulin), ADTRP (Androgen-dependent TFPI-regulating protein), SLC7A8 (Solute carrier family 7 member 8), ITGA11 (Integrin alpha-11), IL1B (Interleukin 1 beta), FLRT3 (Fibronectin leucine rich transmembrane protein 3), THBD (Thrombomodulin), CXCL6 (Chemokine (C-X-C motif) ligand 6), ITGB8 (Integrin beta-8), HGF (Hepatocyte growth factor), CAMKID (Calcium/calmodulin-dependent protein kinase ID), LACC1 (Laccase domain containing 1), GPR68 (G protein-coupled receptor 68), BDKRB2 (Bradykinin receptor B2), NLRC4 (NLR family CARD domain containing 4), SCN1A (Sodium voltage-gated channel alpha subunit 1), ASS1 (Argininosuccinate synthase 1), KCNAB2 (Potassium voltage-gated channel subfamily A beta member 2), SLC6A9 (Solute carrier family 6 member 9), CTSW (Cathepsin W), SYT12 (Synaptotagmin 12), TNFSF13B (Tumor necrosis factor ligand superfamily member 13B), ABCC3 (ATP binding cassette subfamily C member 3), and QPCT (Glutaminyl-peptide cyclotransferase); or (b) a decrease in expression of at least one of EPHA2 (EPH receptor A2), ESM1 (Endothelial cell-specific molecule 1), SLC7A10 (Solute carrier family 7 member 10), HES1 (Hes family bHLH transcription factor 1), WWC1 (WW and C2 domain containing 1), NEDD9 (Neural precursor cell expressed, developmentally down-regulated 9), and IL31RA (Interleukin 31 receptor A).

2. The method according to claim 1, wherein the enhancement of efficacy of the stem cell involves a reduction in size of the stem cell.

3. The method according to claim 1, wherein the enhancement of efficacy of the stem cell comprises at least one of a decrease in size of the stem cell, an improvement in proliferation ability, an improvement in differentiation potency, an improvement in migration ability, and an improvement in angiogenic potential.

4. The method according to claim 1, wherein the enhancement of migration ability of the stem cell comprises:

(a) an increase in expression of at least one of EFNA1, ADAM8, CYP1B1, KDR, ADTRP, SLC7A8, ITGA11, IL1B, FLRT3, THBD, CXCL6, ITGB8, and; and (b) a decrease in expression of at least one of EPHA2, SLC7A10, HES1, WWC1, and NEDD9.

5. The method according to claim 1, wherein the enhancement of immunoregulatory ability of the stem cell comprises:

(a) an increase in expression of at least one of CAMKID, ADAM8, LACC1, GPR68, BDKRB2, NLRC4, IL1B, SCN1A, CXCL6 and ASS1; and (b) a decrease in expression of at least one of EPHA2 and IL313RA.

6. The method according to claim 1, wherein the culturing is performed in a culture medium comprising at least one selected from the group consisting of KSB-3 Basal Medium, Dulbecco's Modified Eagle's Medium (DMEM), Minimal Essential Medium (MEM), Basal Medium Eagle (BME), RPMI 1640, Dulbecco's Modified Eagle's Medium: Nutrient Mixture F-10 (DMEM/F-10), Dulbecco's Modified Eagle's Medium: Nutrient Mixture F-12 (DMEM/F-12), α-Minimal essential Medium (α-MEM), Glasgow's Minimal Essential Medium (G-MEM), Isocove's Modified Dulbecco's Medium (IMDM), Human umbilical vein endothelial growth medium, Adipocyte differentiation medium, Osteocyte differentiation medium, Chondrocyte differentiation medium, and KnockOut DMEM.

7. The method according to claim 1, wherein the diameter of the stem cell cultured on a poly(vinylidene fluoride) (PVDF) membrane in the form of a film formed by electrospinning and having a surface coated with fibronectin is 10.3 um to 18.4 um.

8. A method for producing a cell therapy product, the method comprising obtaining an umbilical cord blood-derived mesenchymal stem cell having enhanced efficacy by culturing the stem cell on a poly(vinylidene fluoride) (PVDF) membrane in the form of a film formed by electrospinning, the PVDF membrane having a surface coated with fibronectin and, (a) increasing the expression of at least one of EFNA1, ADAM8, ANGPTL4, ANGPTL6, CYP1B1, APOD, KDR, EREG, ADTRP, SLC7A8, ITGA11, IL1B, FLRT3, THBD, CXCL6, ITGB8, HGF, CAMK1D, LACC1, GPR68, BDKRB2, NLRC4, SCN1A, ASS1, KCNAB2, SLC6A9, CTSW, SYT12, TNFSF13B, ABCC3 and QPCT; or (b) decreasing the expression of at least one of EPHA2, ESM1, SLC7A10, HES1, WWC1, NEDD9 and IL31RA, wherein the membrane is in form of a film formed by electrospinning.

9. The method according to claim 8, wherein the enhancement of efficacy of the stem cell comprises at least one of a decrease in size of the stem cell, an improvement in proliferation ability, an improvement in differentiation potency, an improvement in migration ability, and an improvement in tube formation ability.

10. The method according to claim 8, further comprising differentiating the stem cell by culturing the obtained stem cell.

* * * * *